United States Patent
Lehmann et al.

(10) Patent No.: US 10,112,964 B2
(45) Date of Patent: Oct. 30, 2018

(54) DITHIOLENE METAL COMPLEX COLORLESS IR ABSORBERS

(71) Applicant: BASF SE, Ludwigshafen (DE)

(72) Inventors: Urs Lehmann, Basel (CH); Daniel Heizler, Basel (CH)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 15/837,371

(22) Filed: Dec. 11, 2017

(65) Prior Publication Data

US 2018/0099988 A1    Apr. 12, 2018

Related U.S. Application Data

(60) Continuation of application No. 15/255,418, filed on Sep. 2, 2016, now Pat. No. 9,738,611, which is a (Continued)

(30) Foreign Application Priority Data

Jan. 17, 2007    (EP) .................................... 07100657

(51) Int. Cl.
| | | |
|---|---|---|
| G02B 5/20 | (2006.01) | |
| C07F 15/04 | (2006.01) | |
| C07D 233/88 | (2006.01) | |
| C07F 15/00 | (2006.01) | |
| B29C 65/16 | (2006.01) | |
| C07D 239/22 | (2006.01) | |
| B29C 65/00 | (2006.01) | |
| B29B 13/02 | (2006.01) | |
| G02B 5/22 | (2006.01) | |
| C07F 11/00 | (2006.01) | |
| C07D 233/86 | (2006.01) | |
| C07D 233/84 | (2006.01) | |
| B29K 81/00 | (2006.01) | |
| B29K 23/00 | (2006.01) | |
| B29C 35/08 | (2006.01) | |

(Continued)

(52) U.S. Cl.
CPC .......... *C07F 15/045* (2013.01); *B29B 13/024* (2013.01); *B29C 65/1677* (2013.01);
(Continued)

(58) Field of Classification Search
CPC ..................................................... G02B 5/208
See application file for complete search history.

(56) References Cited

U.S. PATENT DOCUMENTS 6,926,764 B2    8/2005    Bleikolm et al.
9,260,614 B2    2/2016    Reichelt et al.
(Continued)

FOREIGN PATENT DOCUMENTS

JP    2004045653 A    2/2004
WO    WO-2006/015414 A1    2/2006

OTHER PUBLICATIONS

Additives Aid Laser Welding, Plastic Additives and Compounding, vol. 7, No. 1, Jan. 2005.
(Continued)

*Primary Examiner* — Joseph R Kosack
(74) *Attorney, Agent, or Firm* — Marshall, Gerstein & Borun LLP

(57) ABSTRACT

The invention relates to the use of compounds of formulae (I) and/or (II) as colorless IR absorbers wherein M is Ni, Pd, Pt, Au, Ir, Fe, Zn, W, Cu, Mo, In, Mn, Co, Mg, V, Cr or Ti, $X_1$, $X_2$ and $X_3$ are each independently of the others sulfur or oxygen, $R_1$, $R_2$, $R_3$, $R_4$, $R_5$ and $R_6$ are each independently of the others hydrogen, $NR_7R_8$, unsubstituted or substituted $C_1$-$C_{18}$alkyl, $C_1$-$C_{18}$ alkyl wherein the alkylene chain is interrupted with oxygen, unsubstituted or substituted $C_1$-$C_{18}$alkenyl, unsubstituted or substituted aryl, unsubstituted or substituted arylalkyl or unsubstituted or substituted heteroarylalkyl, $R_7$ and $R_8$, each independently of the other, being unsubstituted or substituted $C_1$-$C_{18}$alkyl, unsubstituted or substituted aryl, unsubstituted or substituted arylalkyl or unsubstituted or substituted heteroarylalkyl, a further IR absorber optionally being added to the compounds of formulae (I) and (II). The invention relates also to novel dithiolene compounds of formulae (I) and (II) wherein $X_1$ is oxygen and $X_2$ and $X_3$ are oxygen or sulfur. The invention relates furthermore to novel dithiolene compounds of formulae (I) and (II) wherein $R_1$ to $R_6$ are $NR_7R_8$.

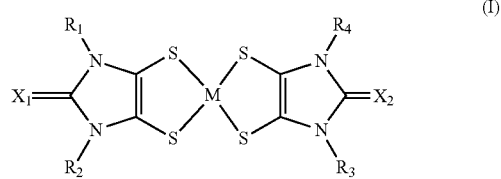

(I)

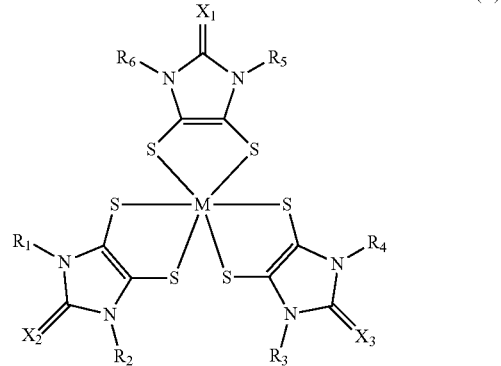

(II)

8 Claims, No Drawings

Related U.S. Application Data division of application No. 12/520,889, filed as application No. PCT/EP2007/064102 on Dec. 18, 2007, now abandoned.

(51) Int. Cl.

| | |
|---|---|
| *B29C 35/02* | (2006.01) |
| *B29K 105/00* | (2006.01) |
| *B29K 69/00* | (2006.01) |
| *B41M 3/14* | (2006.01) |
| *B29K 55/02* | (2006.01) |
| *B29K 67/00* | (2006.01) |
| *B29K 77/00* | (2006.01) |
| *B29K 33/00* | (2006.01) |
| *B29K 27/00* | (2006.01) |
| *B29K 25/00* | (2006.01) |

(52) U.S. Cl.
CPC ............ B29C 66/71 (2013.01); C07D 233/84 (2013.01); C07D 233/86 (2013.01); C07D 233/88 (2013.01); C07D 239/22 (2013.01); C07F 11/00 (2013.01); C07F 15/0066 (2013.01); C07F 15/0093 (2013.01); G02B 5/208 (2013.01); G02B 5/22 (2013.01); G02B 5/223 (2013.01); *B29C 35/0272* (2013.01); *B29C 65/1616* (2013.01); *B29C 65/1674* (2013.01); *B29C 66/7332* (2013.01); *B29C 66/73366* (2013.01); *B29C 66/73921* (2013.01); *B29C 2035/0822* (2013.01); *B29K 2023/12* (2013.01); *B29K 2025/08* (2013.01); *B29K 2027/16* (2013.01); *B29K 2033/08* (2013.01); *B29K 2033/12* (2013.01); *B29K 2055/02* (2013.01); *B29K 2067/00* (2013.01); *B29K 2067/003* (2013.01); *B29K 2067/006* (2013.01); *B29K 2069/00* (2013.01); *B29K 2077/00* (2013.01); *B29K 2081/04* (2013.01); *B29K 2105/0085* (2013.01); *B29K 2105/0088* (2013.01); *B29K 2995/002* (2013.01); *B29K 2995/0017* (2013.01); *B29K 2995/0026* (2013.01); *B29K 2995/0027* (2013.01); *B41M 3/14* (2013.01)

(56) References Cited

U.S. PATENT DOCUMENTS

| | | |
|---|---|---|
| 9,738,611 B2 | 8/2017 | Lehmann et al. |
| 2006/0030704 A1 | 2/2006 | Vonwiller et al. |
| 2017/0285232 A1 | 10/2017 | Lehmann et al. |

OTHER PUBLICATIONS

Patent abstract of JP 2003262953.
Patent abstract of JP 2004045653.
Patent abstract of JP 2005099755.

DITHIOLENE METAL COMPLEX COLORLESS IR ABSORBERS

CROSS-REFERENCE TO RELATED APPLICATION

This is a continuation of U.S. patent application Ser. No. 15/623,699, filed Jun. 15, 2017, which is a continuation of U.S. patent application Ser. No. 15/255,418, filed Sep. 2, 2016, which is a divisional of U.S. patent application Ser. No. 12/520,889, filed Jun. 23, 2009, which is the U.S. national phase of International Application No. PCT/EP2007/064102, filed Dec. 18, 2007, which claims the benefit of European Patent Application No. 07100657.1, filed Jan. 17, 2007.

The invention relates to the use of specific dithiolene metal complexes as colorless IR absorbers. The invention relates also to novel dithiolene metal complexes.

Colorless, or at least barely colored, IR absorbers meet a significant technical need in a wide range of applications, such as security printing (bank notes, credit cards, identity cards, passports etc.), invisible and IR readable bar codes, the laser-welding of plastics, the curing of surface-coatings using IR radiators, the drying and curing of print, the fixing of toners on paper, optical filters for PDPs (plasma display panels), laser marking, the heating of plastics preforms etc.

Several classes of IR absorbers are known, such as, for example, quinone-diimmonium or aminium salts, polymethines (e.g. cyanines, squaraines, croconaines), phthalocyanines and naphthalocyanines, dithiolene and other metal complexes. Newer structures, such as, for example, quaterrylene diimides, have also recently become known.

Also known, besides those organic substances, are inorganic substances such as, for example, lanthanum hexaboride, indium tin oxide (ITO), antimony tin oxide (ATO) in nano-particulate form and coated mica materials ("Lazerflair" from Merck).

Notwithstanding that large number of known compound classes and structures, as yet no IR absorbers have become known that are satisfactory from the technical standpoint. Especially in respect of "colorlessness", that is, minimum inherent color, no truly satisfactory solutions are known that simultaneously meet the other technical stability requirements (heat stability and/or light stability). IR absorbers, for example for security printing, are available, for example, from "American Dye Source", but virtually all of them have an absorption in the VIS range of the spectrum (from 400 to 700 nm).

It has now been found, surprisingly, that a class of heterocyclic dithiolene metal complexes, known per se, is able to meet those requirements. Especially in respect of colorlessness, these compounds are appreciably superior to the known IR absorbers—while simultaneously meeting other technical requirements, such as, for example, good fastness to light (for security printing) or good heat stability when incorporated into plastics material (laser-welding of plastics).

The invention accordingly relates to the use of compounds of formula I and/or II as colorless IR absorbers

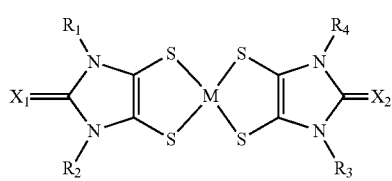

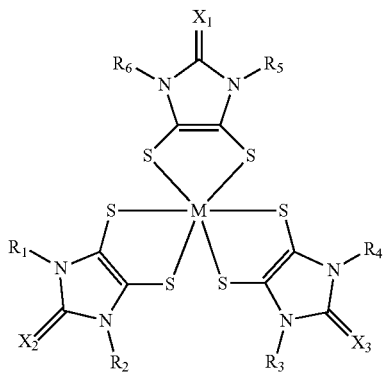

wherein

M is Ni, Pd, Pt, Au, Ir, Fe, Zn, W, Cu, Mo, In, Mn, Co, Mg, V, Cr or Ti, $X_1$, $X_2$ and $X_3$ are each independently of the others sulfur or oxygen, $R_1$, $R_2$, $R_3$, $R_4$, $R_5$ and $R_6$ are each independently of the others hydrogen, $NR_7R_8$, unsubstituted or substituted $C_1$-$C_{18}$alkyl, $C_1$-$C_{18}$ alkyl wherein the alkylene chain is interrupted with oxygen, unsubstituted or substituted $C_1$-$C_{18}$alkenyl, unsubstituted or substituted aryl, unsubstituted or substituted arylalkyl or unsubstituted or substituted heteroarylalkyl, $R_7$ and $R_8$, each independently of the other, being unsubstituted or substituted $C_1$-$C_{18}$alkyl, unsubstituted or substituted aryl, unsubstituted or substituted arylalkyl or unsubstituted or substituted heteroarylalkyl, a further IR absorber optionally being added to the compounds of formulae I and II.

Preference is given to compounds of formula I wherein the metal M is Ni, Pd or Pt. (claim 2)

If the substituents $R_1$ to $R_6$ or $R_1$ to $R_4$ are $C_1$-$C_{18}$alkyl radicals they are preferably unsubstituted $C_1$-$C_{18}$alkyl radicals, more preferably $C_1$-$C_8$alkyl radicals, including straight-chain and branched and also cyclic alkyl radicals. The following may be mentioned as examples: propyl, isopropyl, n-butyl, sec-butyl, tert-butyl, n-hexyl, 2-ethylhexyl, n-octyl, cyclopentyl, cyclohexyl.

If the substituents $R_1$ to $R_6$ or $R_1$ to $R_4$ are $C_1$-$C_{18}$alkyl radicals wherein the alkylene chain is interrupted with oxygen, they are preferably —$(CH_2)_n$—[O—$(CH_2)_m]_k$—$OCH_3$ with n=2-6, m=2 or 3, k=1-6.

If the substituents $R_1$ to $R_6$ or $R_1$ to $R_4$ are $C_1$-$C_{18}$alkenyl radicals they are preferably unsubstituted $C_1$-$C_{18}$alkenyl radicals, more preferably $C_1$-$C_6$alkenyl radicals. Examples may be vinyl or allyl.

If the substituents $R_1$ to $R_6$ or $R_1$ to $R_4$ are aryl groups, they are preferably unsubstituted aryl groups, for example, phenyl, naphthyl, anthryl or phenanthryl groups.

If the substituents $R_1$ to $R_6$ or $R_1$ to $R_4$ are arylalkyl groups, they are preferably unsubstituted arylalkyl groups, for example, —$(CH_2)_q$-phenyl with q=1-6, especially benzyl, ethylphenyl, propylphenyl.

If the substituents $R_1$ to $R_6$ or $R_1$ to $R_4$ are heteroarylalkyl radicals they are preferably unsubstituted heteroarylalkyl radicals which denotes that a heteroaromatic ring is bonded directly to an alkyl group. The heteroaromatic ring is, for example, imidazolyl, pyridyl, thienyl, furyl, thiazolyl, indolyl, quinolinyl, pyrazolyl, pyrazyl, pyridazyl or pyrimidinyl.

The substituents $R_1$ to $R_6$ or $R_1$ to $R_4$ are preferably unsubstituted $C_1$-$C_{18}$alkyl, —$(CH_2)_n$—[O—$(CH_2)_n]_k$—$OCH_3$ with n=2-6, m=2 or 3, k=1-6, unsubstituted $C_1$-$C_{18}$alkenyl, unsubstituted arylalkyl or —$N(C_1$-$C_6$ alkyl$)_2$.

The substituents $R_7$ and $R_8$ are preferably $C_1$-$C_6$alkyl radicals.

In a preferred embodiment compounds of the formula I are used as colorless IR absorber wherein M is Ni, Pd, Pt, $X_1$, $X_2$ and $X_3$ are each independently of the others sulfur or oxygen, $R_1$, $R_2$, $R_3$, $R_4$ are each independently of the others —$N(C_1$-$C_6$alkyl$)_2$, unsubstituted $C_1$-$C_8$alkyl, —$(CH_2)_n$—[O—$(CH_2)_m]_k$—$OCH_3$ with n=2-6, m=2 or 3, k=1-6; vinyl or allyl, —$(CH_2)_q$-phenyl with q=1-6. (Claim 3)

Of particular interest are the structures Ia to Ih.

Ia

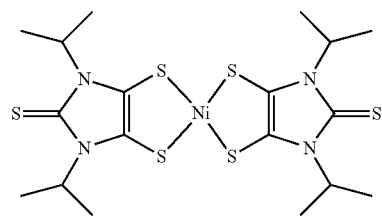

Ib

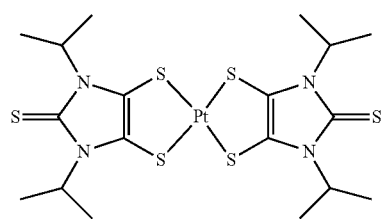

Ic

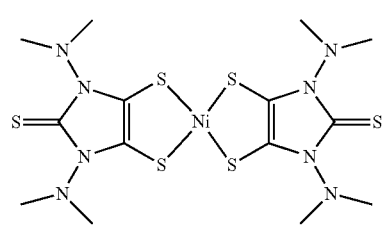

Id

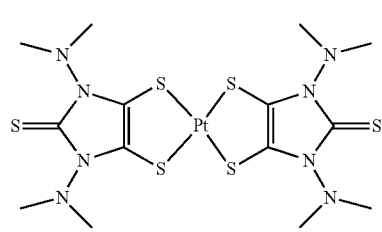

Ie

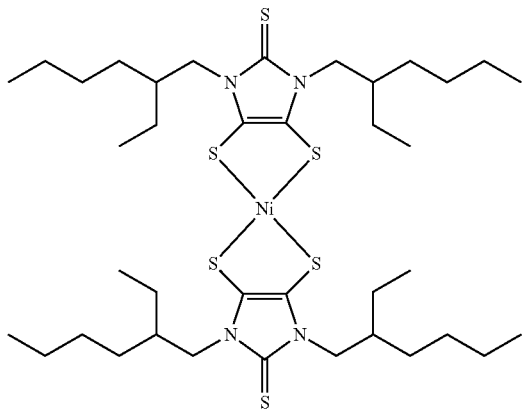

If

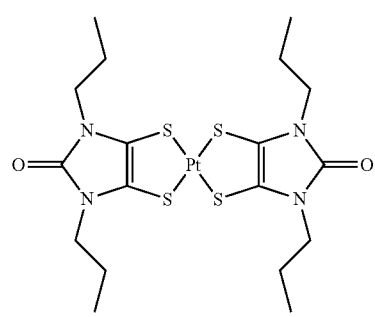

Ig

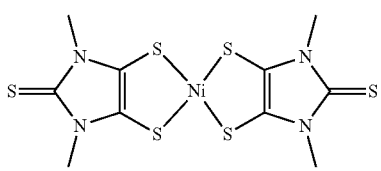

Ih

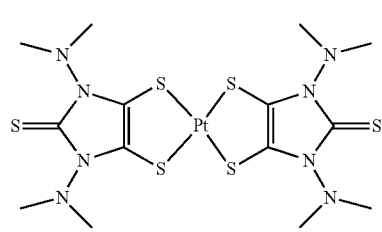

(Claim 4)

Colorless IR absorbers can be used in all fields of application that depend on the IR absorber's remaining invisible. The following uses may be mentioned by way of example: security printing (bank notes, credit cards, identity cards, passports etc.), invisible and IR readable bar codes, the laser-welding of plastics, the curing of surface-coatings using IR radiators, the drying and curing of print, the fixing of toners on paper, laser marking (plastics materials, paper, wood etc.) and the heating of plastics preforms. (Claim 5)

An especially suitable field of application is the use of the compounds of formula I and/or II in security printing and in the laser-welding of plastics material. (Claim 6)

In another embodiment the compounds of formulae I and II are used in security printing and printing of bar codes. (claim 7)

The IR absorbers of formulae I and II can also be in the form of mixtures with further known IR absorbers, especially mixtures with polymethines (cyanines, squaraines and croconaines). Such IR absorber mixtures are suitable especially for security printing. (claim 8)

Examples of preferred polymethines are listed in the following Tables:

Cyanines

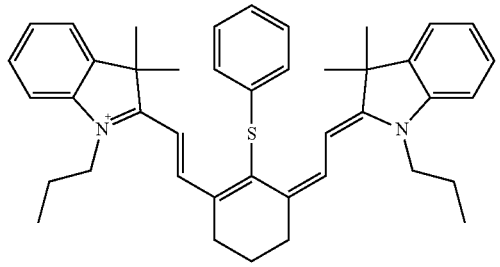

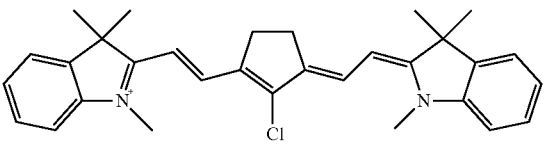

Squaraines

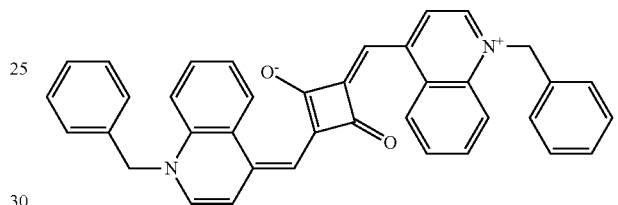

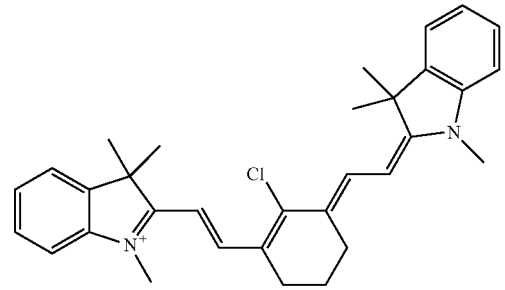

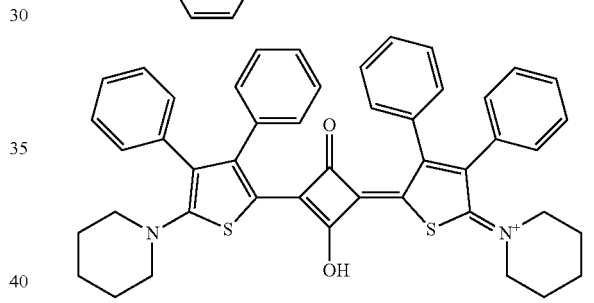

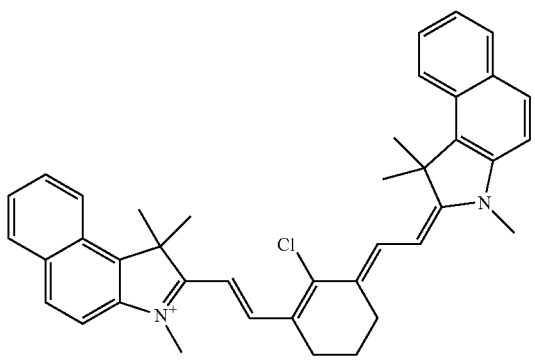

Croconaines

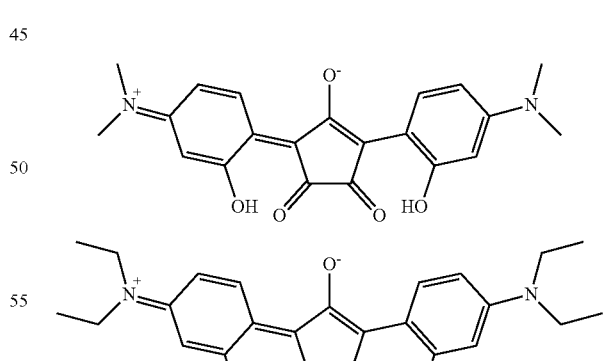

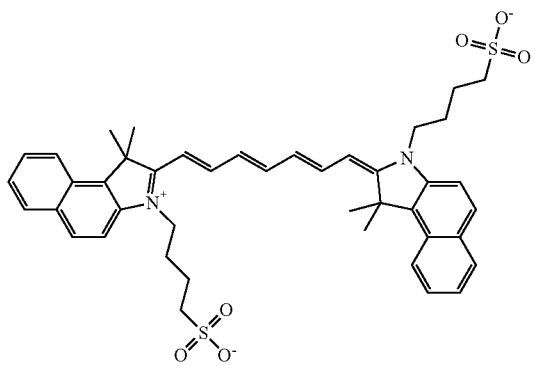

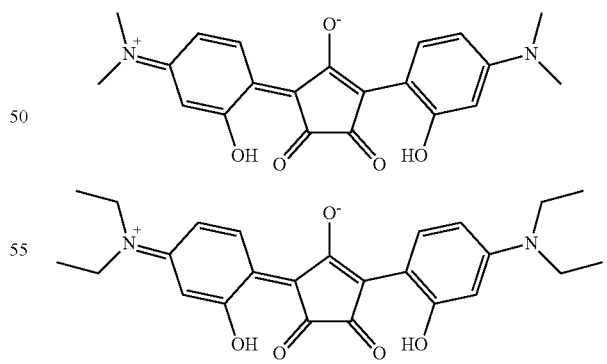

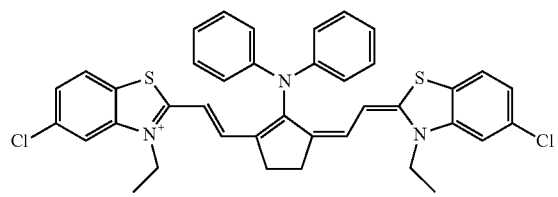

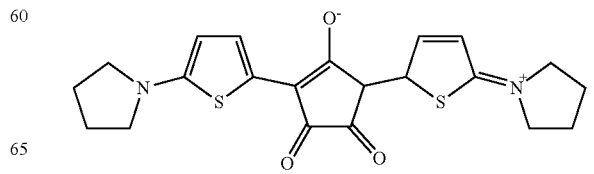

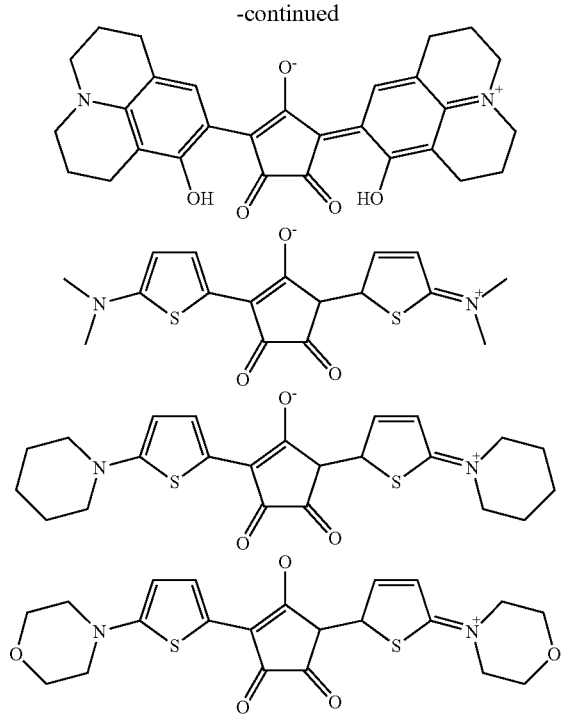

The IR absorbers are used in a concentration of from 10 ppm to 10%, preferably 100 ppm to 2% depending on the chosen application.

The laser welding is preferably carried out using an ND:YAG laser at 1064 nm or using a diode laser at 980 nm or 940 nm, and the concentration of IR absorber is, for example, from 5 to 500 ppm, preferably from 10 to 100 ppm.

In laser welding, plastics components are welded to one another. The dithiolenes according to the invention are suitable especially for welding transparent plastics materials, such as polypropylene, polyvinylbutyral, polyamide, polycarbonate, polycarbonate-polyethylene terephthalate blends, polycarbonate-polybutylene terephthalate blends, polycarbonate-acrylonitrile-styrene-acrylonitrile copolymer blends, polycarbonate-acrylonitrile-butadiene-styrene copolymer blends, polymethyl methacrylate-acrylonitrile-butadiene-styrene co-polymer blends (MABS), polyethylene terephthalate, polybutylene terephthalate, polymethyl methacrylate, polybutyl acrylate, polymethyl methacrylate-polyvinylidene difluoride blends, acrylonitrile-butadiene-styrene copolymers (ABS), styrene-acrylonitrile copolymers (SAN) and polyphenylene sulfone and also mixtures thereof.

Especially advantageous in welding is the use of two identically transparent plastics workpieces, for example colorless-transparent/colorless-transparent or colored-transparent/colored-transparent.

In security printing, the IR absorber is added to the printing ink. Suitable printing inks are water-based, oil-based or solvent-based printing inks, based on pigment or dye, for inkjet printing, flexographic printing, screen printing, intaglio printing, offset printing, laser printing or letterpress printing and for use in electrophotography.

The invention relates also to novel dithiolene compounds of formulae I and II wherein M is Ni, Pd, Pt, Au, Ir, Fe, Zn, W, Cu, Mo, In, Mn, Co, Mg, V, Cr or Ti, $X_1$ is oxygen and $X_2$ and $X_3$ are oxygen or sulfur, $R_1$, $R_2$, $R_3$, $R_4$, $R_5$ and $R_6$ are each independently of the others hydrogen, $NR_7R_8$, unsubstituted or substituted $C_1$-$C_{18}$alkyl, $C_1$-$C_{18}$ alkyl wherein the alkylene chain is interrupted with oxygen, unsubstituted or substituted $C_1$-$C_{18}$alkenyl, unsubstituted or substituted aryl, unsubstituted or substituted arylalkyl or unsubstituted or substituted heteroarylalkyl, $R_7$ and $R_8$, each independently of the other, being unsubstituted or substituted $C_1$-$C_{18}$alkyl, unsubstituted or substituted aryl, unsubstituted or substituted arylalkyl or unsubstituted or substituted heteroarylalkyl.

Those compounds are obtained from the corresponding sulfur compounds ($X_1$, $X_2$, $X_3$=S) by oxidation with a suitable solvent or as described by the examples.

The following compounds may be mentioned by way of example:

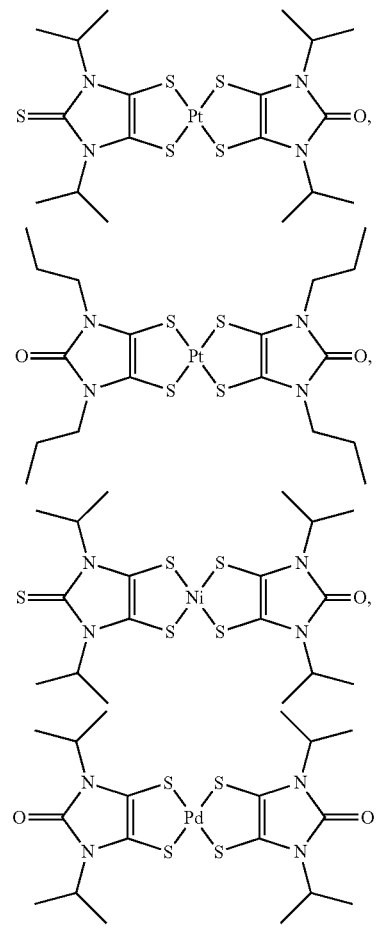

The invention relates also to novel dithiolene compounds of formulae I and II wherein M is Ni, Pd, Pt, Au, Ir, Fe, Zn, W, Cu, Mo, In, Mn, Co, Mg, V, Cr or Ti, $X_1$, $X_2$ and $X_3$ are each independently of the others sulfur or oxygen, $R_1$, $R_2$, $R_3$, $R_4$, $R_5$ and $R_6$ are $NR_7R_8$, wherein $R_7$ and $R_8$ are each independently of the other unsubstituted or substituted $C_1$-$C_{18}$alkyl, unsubstituted or substituted aryl, unsubstituted or substituted arylalkyl or unsubstituted or substituted heteroarylalkyl.

Preferably —$NR_7R_8$ is —$N(C_1$-$C_6alkyl)_2$

The following compounds Ic and Id may be mentioned by way of example:

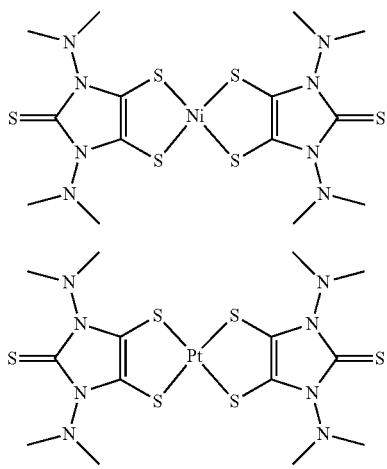

Ic

Id

The novel dithiolene compounds, like the known dithiolene compounds, are suitable for use in security printing (bank notes, credit cards, identity cards, passports etc.), invisible and IR readable barcodes, the laser-welding of plastics, the curing of surface-coatings using IR radiators, the curing and drying of print, the fixing of toners on paper, laser marking (plastics, paper, wood etc.) and the heating of plastics preforms etc.

Additionally, the novel dithiolene compounds of formulae I and II are suitable for use as optical filters for plasma display panels (PDPs). For this application absorption below 1000 nm, especially around 900 nm, is of special interest.

EXAMPLES

Example 1 Preparation of

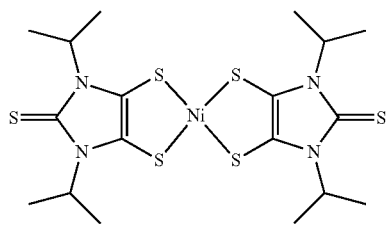

The compound is known from J. Chem. Soc., Dalton Trans 1998, 3731-3736, and its preparation is described therein.

1,3-Diisopropyl-4,5-dioxo-imidazoline-2-thione is reacted under reflux conditions with metallic nickel and Lawesson's reagent

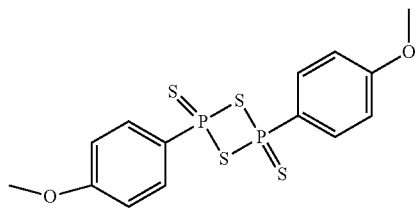

in chlorobenzene.
Absorption maximum (chloroform): 1001 nm (79 000)

Example 2 Preparation of

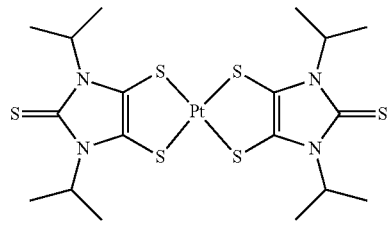

Reaction is carried out analogously to Example 1, with platinum dichloride and Lawesson's reagent.

Absorption maximum (chloroform): 1000 nm (113 000).

Example 3a Preparation of

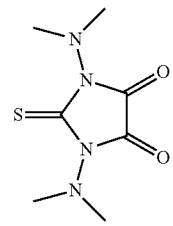

12.26 parts of N,N-dimethylhydrazine are added at room temperature, with stirring, to a solution of 7.65 parts of carbon disulfide in 250 parts of dichloroethane. The temperature is then increased to 40° C. and stirring is carried out for 16 hours at that temperature to complete the reaction. The temperature is subsequently increased to 80° C. for one hour.

A further 750 parts of dichloroethane are then added, and 13.88 parts of oxalyl chloride (dissolved in a small amount of dichloroethane) are added dropwise over a period of 90 minutes. The reaction mixture is then heated to reflux and maintained at reflux for 2 hours, after which it is concentrated and the yellow crystals are filtered off and washed with a small amount of dichloroethane. After drying, 14 parts of product having the structure indicated above are obtained.

Example 3b Preparation of

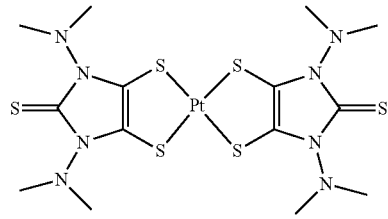

0.333 part of platinum dichloride is added to a solution of 0.541 part of the product from example 3a and 1.085 parts of Lawesson's reagent in 50 parts of toluene. The reaction mixture is maintained at 110° C. for 90 minutes and filtered while hot, and 500 parts of n-hexane are added to the filtrate after cooling. The resulting precipitate is filtered off and dried, yielding 0.5 part of product (absorption maximum 994 nm).

Example 4

The procedure is analogous to that in the previous examples, except that the metal used is molybdenum, thus yielding the corresponding 1:3 molybdenum complex:

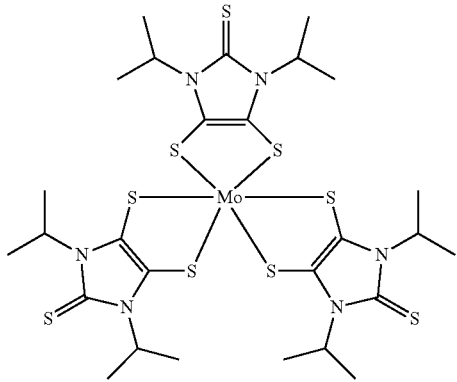

Example 5 Preparation of

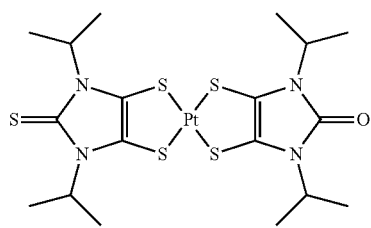

The compound from Example 2 is oxidised with atmospheric oxygen in dichloromethane at reflux temperature to form the corresponding oxo compound. Its absorption maximum is found at 968 nm.

Example 6a Preparation of

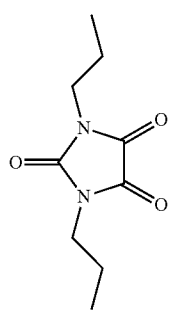

29.14 parts of 1,3-di-n-propyl-urea are dissolved in 300 parts of toluene at 40° C. Over a period of 40 minutes 27.18 parts of oxalyl chloride are added at 80° C. to the stirred solution. After a further hour of stirring at 100° C. the solution is evaporated at 60° C. to dryness: 36.8 parts of the product are obtained.

Example 6b Preparation of

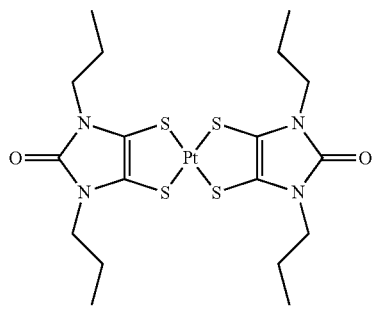

1.59 parts of the product from Example 6a, 1.06 parts of platinum dichloride and 3.47 parts of Lawesson's reagent are heated to 110° C. under nitrogen in 100 parts of toluene. After 45 minutes reaction time the dark solution is cooled down to −10° C. and the precipitation is filtered off, washed with ethanol and some acetone. For purification the crude product is dissolved in dichloromethane and precipitated slowly by addition of methanol. Dark blue crystals are collected by filtration. The absorption maximum of the product is found at 900 nm (chloroform).

Example 7 Preparation of

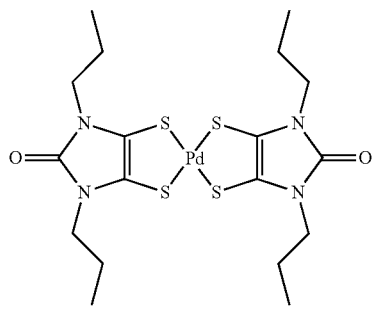

Proceeding analogously to Example 6b but using palladium chloride instead of platinum chloride the corresponding palladium complex with an absorption maximum of 921 nm is obtained.

Example 8 Preparation of

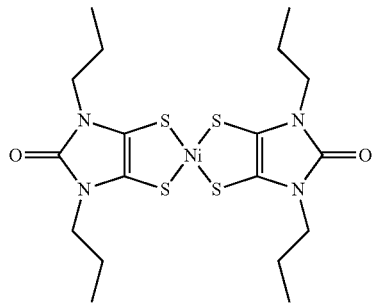

Proceeding analogously to Example 6b but using metallic nickel instead of platinum chloride the corresponding nickel complex with an absorption maximum of 891 nm is obtained.
Example 9 to 24
Compounds of Examples 9 to 24 (structures given in the table below) are obtained by analogous procedures as described in Examples 1 to 8:
| Example | |
|---|---|
| 9 | 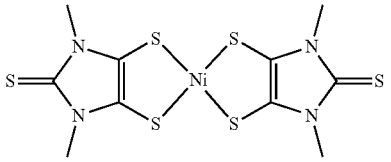<br>990 nm |
| 10 | 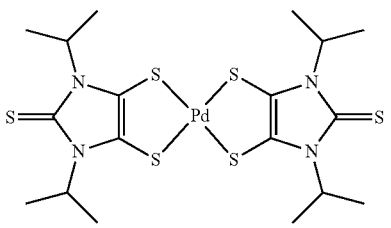<br>1020 nm |
| 11 | 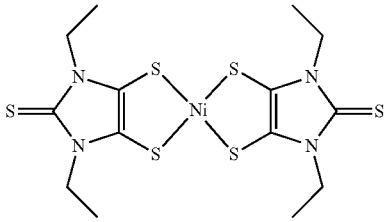<br>996 nm |
| 12 | 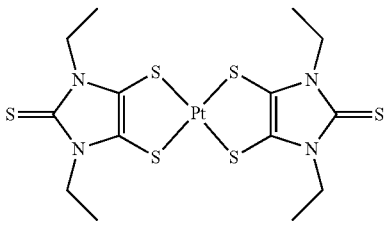<br>999 nm |
| 13 | 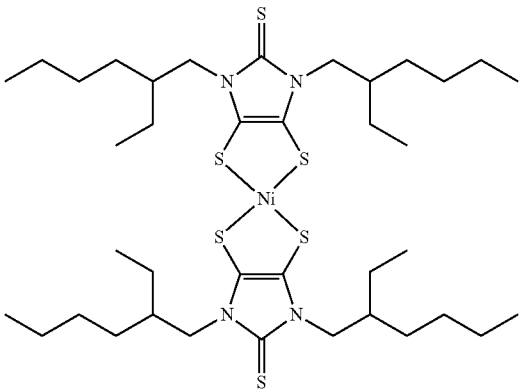<br>1009 nm |

-continued
| Example | |
|---|---|
| 14 | 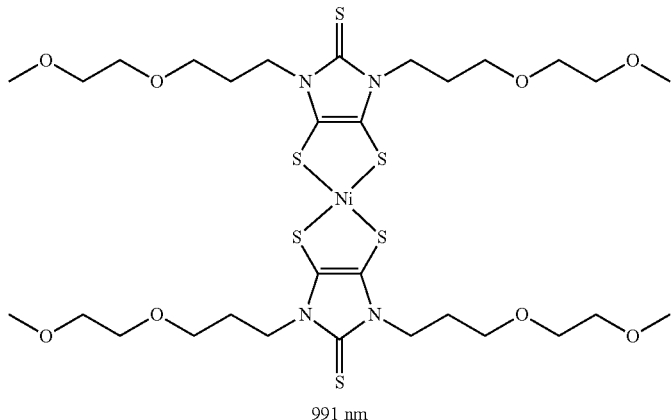
991 nm |
| 15 | 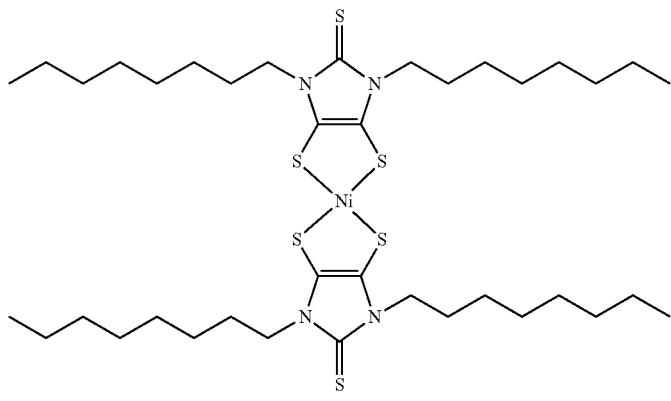
1002 nm |
| 16 | 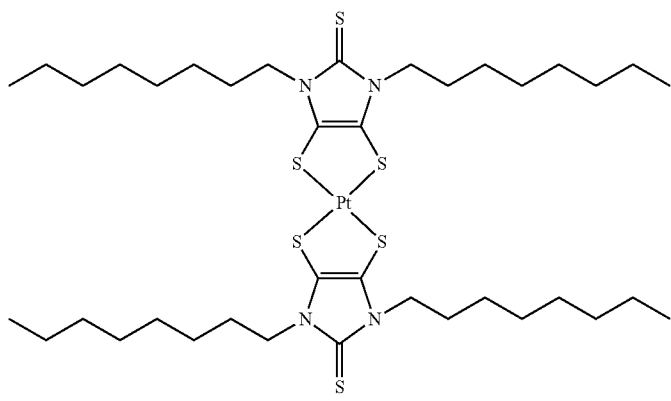
1007 nm |
| 17 | 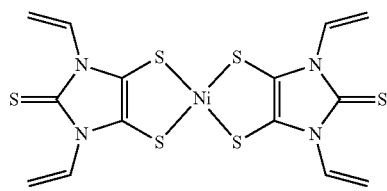
1006 nm |

| Example | |
|---|---|
| 18 | 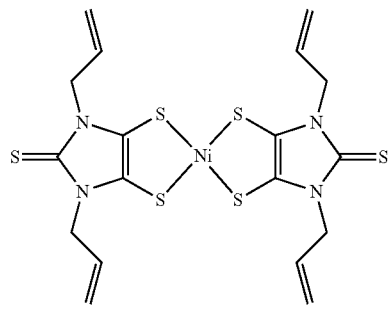<br>1003 nm |
| 19 | 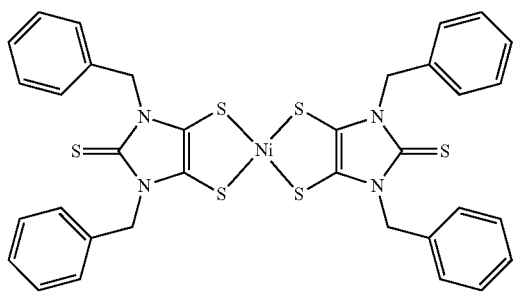<br>1011 nm |
| 20 | 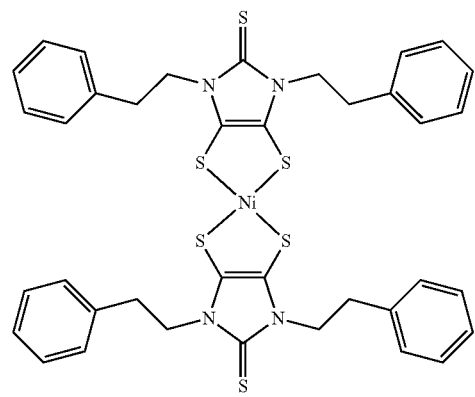<br>1007 nm |
| 21 | 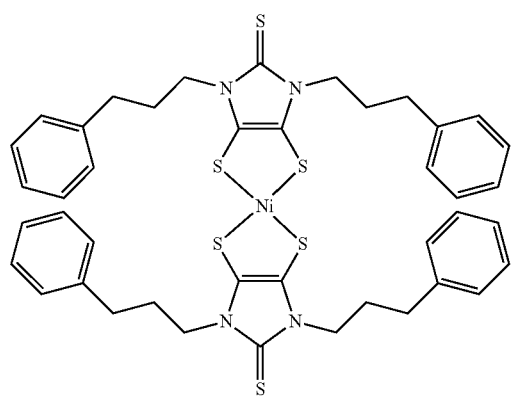<br>1003 nm |

| Example | |
|---|---|
| 22 | 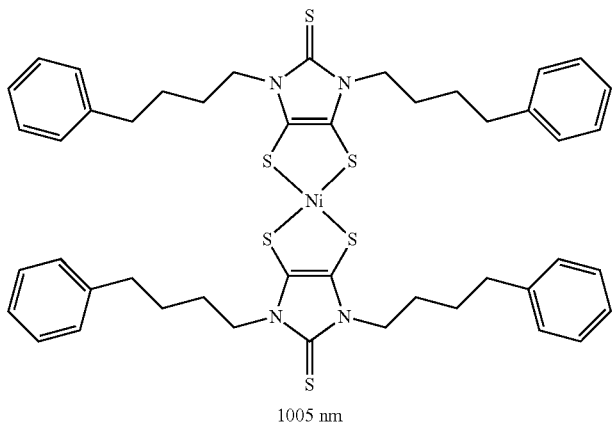
1005 nm |
| 23 | 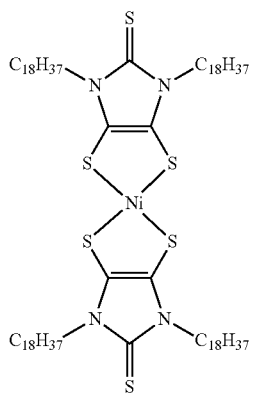
1002 nm |
| 24 | 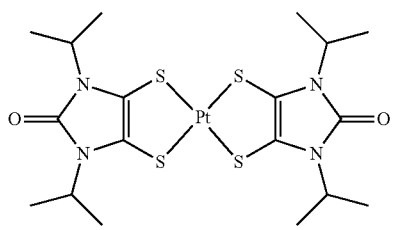
903 nm |

APPLICATION EXAMPLES

Example A1 (Security Printing)

11.9 parts of vinyl chloride, 2.1 parts of vinyl acetate, 10 parts of ethoxypropanol, 75.5 parts of methyl ethyl ketone and 0.5 part of the product from Example 1 are shaken together with 150 g of glass beads for 30 minutes in a Skandex mixer.

The resulting printing ink is applied to contrast paper using a doctor blade (film thickness when damp: 6 μm). The print is visually colorless, but is clearly visible in the IR range using an IR-viewing device (cut-off filter 715 nm). The fastness to light is excellent.

Example A2 (Security Printing)

By proceeding as indicated in Example A1 but using the IR absorber from Example 2, there accordingly is likewise obtained a colorless print having excellent fastness to light, which is clearly visible in the infrared range using an IR-viewing device.

Example A3 (Laser-Welding of Plastics Material)

Using an injection-moulding machine, the IR absorber from Example 1 is incorporated into a polycarbonate disc having a thickness of 2 mm (concentration: 100 ppm). Using an Nd:YAG laser, the resulting, virtually colorless disc is welded at a power of 30 watt and a rate of advance of 20 mm/s to a second 1 mm-thick pure polycarbonate disc not containing IR absorber. The resulting weld is characterised by an excellent bond, unchanged transparency, no melt irruptions and no bubbling. Under heavy mechanical loading, breakage of the discs does not occur at the welded seam.

Example A4 (Laser-Welding of Plastics Material)

By proceeding as indicated in Example A3 but using the IR absorber from Example 2, a virtually colorless polycarbonate disc is likewise obtained which has excellent welding properties. The resulting weld has unchanged transparency, the welding leaves no melt irruptions or bubbling and the strength of the weld is excellent.

Examples A5 and A6

By proceeding as indicated in Examples A3 and A4 but, instead of using an Nd:YAG laser (1064 nm), using a diode laser having an emission wavelength of 980 nm, similarly good results to those described in Examples A3 and A4 are obtained.

Examples A7 and A8

By proceeding as indicated in Examples A3 and A4 but, instead of using an Nd:YAG laser (1064 nm), using a diode laser having an emission wavelength of 940 nm, a comparably good weld is obtained at a laser power of 80 watt.

Example A9

By proceeding as indicated in Example A3, but using polypropylene discs having a thickness of 1.5 mm, the welds obtained are likewise very good.

The invention claimed is:

1. A method of using colorless IR absorbers comprising
   a) treating a material with a compound from the group consisting of

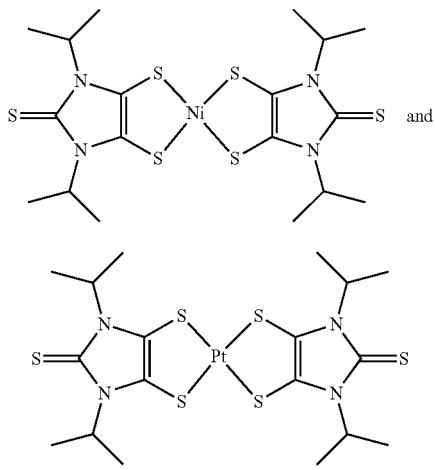

Ia

Ib wherein the material is a security print, an invisible and IR readable bar code,
a laser-welded plastic, a dried print, a fixed toner on paper, a laser marked plastic, or a heated preform,
optionally a further IR absorber; and
b) using the treated material of a) for security printing, invisible and IR readable bar codes, laser-welding of plastics, drying of print, fixing of toners on paper, laser marking, and heating of plastics preforms.

2. The method according to claim 1, wherein step b) is using the treated material for laser-welding of plastics.

3. The method according to claim 1, wherein step b) is using the treated material for security printing or producing invisible and IR readable bar codes.

4. The method according to claim 1, wherein the further IR absorbers are polymethines.

5. A method of using colorless IR absorbers comprising
   a) treating a material with a compound selected from the group consisting of

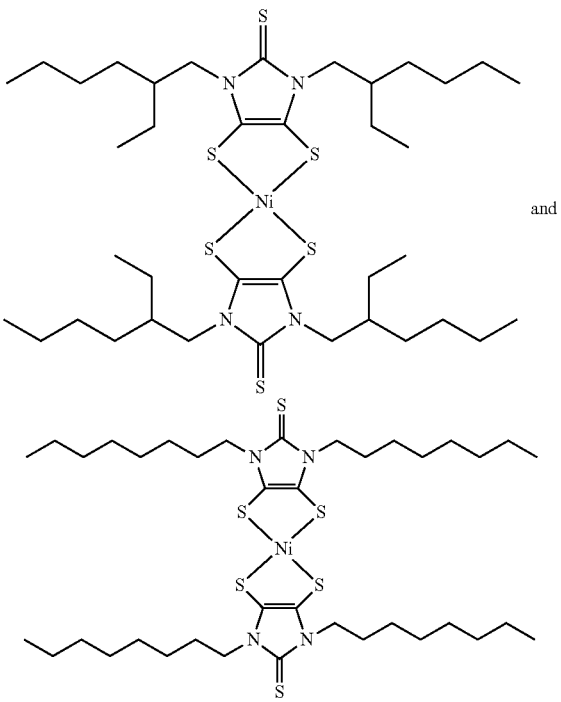

and wherein the material is a security print, an invisible and IR readable bar code,
a laser-welded plastic, a dried print, a fixed toner on paper, a laser marked plastic, or a heated preform,
optionally a further IR absorber; and
b) using the treated material of a) for security printing, invisible and IR readable bar codes, laser-welding of plastics, drying of print, fixing of toners on paper, laser marking, and heating of plastics preforms.

6. The method according to claim 5, wherein step b) is using the treated material for laser-welding of plastics.

7. The method according to claim 5, wherein step b) is using the treated material for security printing or producing invisible and IR readable bar codes.

8. The method according to claim 5, wherein the further IR absorbers are polymethines.

* * * * *